United States Patent [19]

Atad

[11] Patent Number: 4,976,692
[45] Date of Patent: Dec. 11, 1990

[54] CATHETER PARTICULARLY USEFUL FOR INDUCING LABOR AND/OR FOR THE APPLICATION OF A PHARMACEUTICAL SUBSTANCE TO THE CERVIX OF THE UTERUS

[75] Inventor: Jack Atad, Haifa, Israel

[73] Assignee: Travenol Laboratories (Israel) Ltd., Ashdod, Israel

[21] Appl. No.: 411,987

[22] Filed: Sep. 25, 1989

[51] Int. Cl.$^5$ .............................................. A61M 29/00
[52] U.S. Cl. ...................................... 604/101; 604/55
[58] Field of Search ............... 604/101, 102, 103, 104, 604/96, 97, 55, 53, 54

[56] References Cited

U.S. PATENT DOCUMENTS 4,664,114  5/1987  Ghodsian ........................... 604/101
4,693,704  9/1987  Ogita ................................... 604/101

FOREIGN PATENT DOCUMENTS 2454589  6/1975  Fed. Rep. of Germany ...... 604/101

Primary Examiner—John D. Yasko
Attorney, Agent, or Firm—Benjamin J. Barish

[57] ABSTRACT

Artificial ripening of the unfavorable cervix was attempted in 69 patients by a newly designed double balloon catheter, placed in the cervix for 12 hours. The balloons, such inflated to 40 ml, covered the internal and external cervical os, with the catheter's opening located between them, in the endocervical canal. The study was carried out in three phases. In the first phase, 22 term pregnant women received intracervical PGE2 gel through the catheter with two inflated balloons confining the gel to the cervix. The second phase consisted of a double blind randomized controlled study, where, through the double balloon catheter, ten women received PGE2 gel and another ten were given placebo gel. The third phase consisted of an open study of inserting the catheter alone, without PGE2, and inflation of the balloons in 27 patients. A substantial mean increases in the Bishop Score was noted in all these phases.

12 Claims, 1 Drawing Sheet

CATHETER PARTICULARLY USEFUL FOR INDUCING LABOR AND/OR FOR THE APPLICATION OF A PHARMACEUTICAL SUBSTANCE TO THE CERVIX OF THE UTERUS

BACKGROUND AND OBJECTS OF THE INVENTION

The present invention relates to a catheter particularly useful for inducing labor and/or for the application of a pharmaceutical substance to the cervix of the uterus.

It has been shown recently that a certain pharmaceutical substance, namely prostaglandin (PG), leads to local biochemical and biophysical alterations in the cervical region that have the effect of reducing cervical resistance in addition to inducing myometrial contractions. Endocervical application of this substance in a gel has been gaining increasing acceptance for priming the cervix before the induction of labour or for the induction of labour. A pre-manufactured mixture of 0.5 mg $PGE_2$ and 2.5 mm triacetin gel ("Prepidil Gel", supplied by Upjohn, Crawley) is now available, and recent trials exhibited no gel-specific problems relating to stability, homogeneity or sterility.

At the present time, the Prepidil Gel is applied by intra-cervical injection using a syringe with a simple canula. However, it is extremely difficult, if not impossible, to administer 3 ml of gel in a strictly endocervical fashion without applying some of the gel retroamniotically, and without having some flowing back out of the cervical canal to the vagina.

An object of the present invention is to provide a catheter particularly useful for this purpose.

During clinical studies made with the above-described catheter it was surprisingly discovered that merely the insertion of the catheter without the delivery of the pharmaceutical substance also had the effect in many cases of artificially ripening the cervix and inducing labor.

Accordingly, another object of the present invention is to provide a catheter which may be used for inducing labor by merely inserting the catheter as described above and without the delivery of the phamaceutical substance.

Further objects of the present invention are to provide a method of inducing labor in a female, and also a method of applying a pharmaceutical substance directly to the cervical canal of a female.

BRIEF SUMMARY OF THE INVENTION

According to one aspect of the present invention, there is provided a catheter particularly useful for application to the cervix of the uterus in order to induce labour, comprising: a slender, flexible tube open at one end and closed at the opposite end; an inflatable distal balloon fixed to the tube at its closed end and adapted to be received in the uterus; an inflatable proximal balloon fixed to the tube at a location spaced a small distance from the distal balloon in the direction towards the open end of the tube and adapted to be received in the vagina, with the connecting portion of the tube between the two balloons passing through the cervical canal; inlet means at the open end of the tube connected by conduit means leading to the two balloons for inflating each balloon after positioned in the uterus and vagina, respectively further inlet means at the open end of the tube for introducing a pharmaceutical substance; and an outlet opening in the connecting portion of the tube between the two balloons delivering the pharmaceutical substance to the cervical canal.

According to another aspect of the present invention, there is provided a method of inducing labor comprising introducing the above-described catheter into the birth canal of the female with the distal balloon located in the uterus and the proximal balloon located in the vagina, and inflating both balloons.

In the preferred embodiment of the invention described below, the proximal balloon is spaced about 20 mm from the distal balloon; also, the discharge opening has a longer length, e.g., 5 mm, than a width, e.g., 2 mm.

Further features and advantages of the invention will be apparent from the description below

BRIEF DESCRIPTION OF THE DRAWINGS

The invention is herein described, by way of example only, with reference to the accompanying drawings, wherein.

DESCRIPTION OF A PREFERRED EMBODIMENT

Figure 1:
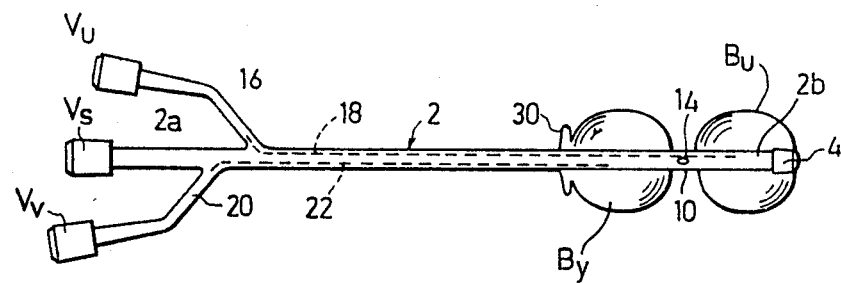
FIG. 1 illustrates one form of catheter constructed in accordance with the present invention.

The catheter illustrated in FIG. 1 comprises a slender, flexible tube 2 open at one end 2a and closed at its opposite end 2b by a plug 4 fixed within that end of the tube. The illustrated catheter further includes an inflatable distal balloon $B_u$ fixed to the tube at its closed end 2b, and a second inflatable balloon $B_v$ fixed to the tube 2 at a location spaced a relatively small distance from balloon $B_u$ in the direction towards the open end 2a of the tube. Balloon $B_u$, hereinafter sometimes referred to as the distal balloon, is adapted to be received in the uterus of the female; and balloon $B_v$, hereinafter sometimes referred to as the proximal balloon, is adapted to be received in the cervico-vagina, with the connecting portion 10 of the tube between the two balloons passing through the cervical canal. This connecting portion 10 of the tube is formed with an outlet opening 14, preferably of an oblong configuration, having a length larger than its width.

The distal balloon $B_u$ to be received in the uterus is inflatible by a fluid, (e.g., sterilized saline water), introduced via an inlet 16 adjacent the open end 2a of the tube 2 under the control of a valve $V_u$ and fed to the balloon via conduit 18 integrally formed with tube 2. Similarly, the proximal balloon $B_v$ to be received in the cervico-vagina is adapted to be inflated by a fluid (e.g. sterilized saline water) introduced via inlet 20 under the control of a valve $V_v$ and fed to balloon $B_v$ via a second conduit 22 integrally formed with the tube. The pharmaceutical substance to be applied directly to the cervical canal is introduced via the open end 2a of tube 2, optionally under the control of a valve $V_s$, and is fed through the tube to the outlet opening 14 when located in the cervical canal.

FIG. 1 also illustrates the inclusion of a palpable demarcation ring located on the proximal side of the vaginal balloon $B_v$. This ring enables correct positioning of the catheter by palpation, even without cervical visualization. Thus, the catheter may be inserted into the birth canal of the female while the female lies supine in bed, thereby avoiding the discomfort with the lithotomy position and and the insertion of a vaginal speculum.

Figure 2:
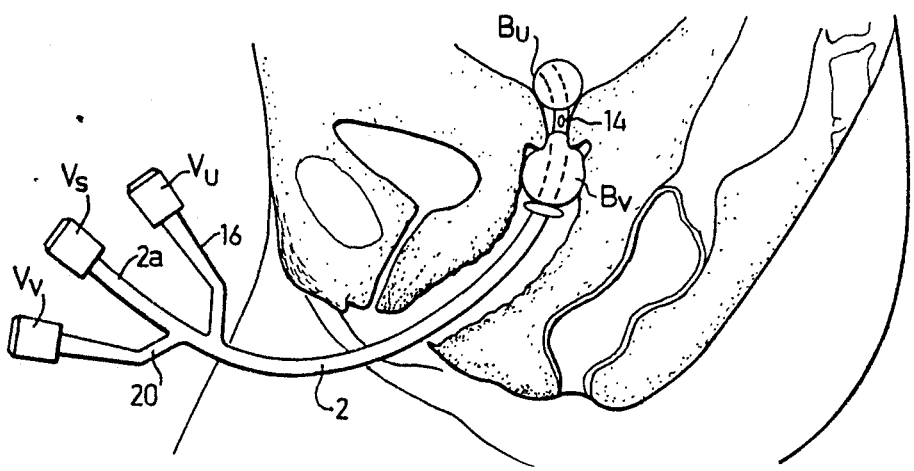
FIG. 2 is a diagram illustrating the manner of using the catheter of FIG. 1 for inducing labor and/or for the application of a pharmaceutical substance directly to the cervical canal.

The manner of using the catheter illustrated in the drawings is more particularly illustrated in FIG. 2.

Thus, while both of the balloons $B_u$ and $B_{cv}$ are deflated, the catheter is introduced into the birth canal of the female patient until the distal balloon $B_u$ is located within the uterus. Distal balloon 6 is then inflated by applying a fluid, e.g., saline water, via Valve $V_u$ inlet 16 and conduit 18. The catheter is then manipulated (e.g., withdrawn slightly if necessary) to locate the deflated proximal balloon $B_{cy}$ within the vagina, and that balloon is then inflated by introducing saline water via its inlet 20 and its conduit 22. This positions the connecting portion 10 of the tube 2 in the cervical canal at the entrance to the uterus. The pharmaceutical substance is then applied via the open end 2a of tube 2, and via the outlet opening 14 in the connecting portion 10 of the tube directly to the cervical canal.

The catheter is not to be removed from its position until the onset of labour or spontaneous rupture of the membranes.

It will thus be seen that the use of the illustrated catheter enables the pharmaceutical substance, such as the above-mentioned pre-manufactured mixture of 0.5 mg $PGE_2$ and 2.5 ml triacetin gel ("Prepidil Gel"), to be applied in a more precise manner with no leakage and with substantially no flowback out of the cervical canal to the vagina.

The illustrated catheter was used for the induction of labour in women with unriped cervix (Bishop score 4 or less), and it was found that this technique was well tolerated by the patients and easy to perform. It was also surprisingly found that the insertion, in the manner described above, of the catheter alone, i.e., without introducing the above-mentioned pharmaceutical substance, also had the effect of articifially ripening the cervix and thereby inducing labor.

As one example, the illustrated catheter may have a length of 350 mm, an inner diameter of 3.5 mm, an outer diameter of 5.9 mm, the length of the connecting portion 10 between the two balloons 6, 8, may be 20 mm, and the outlet opening 14 may be 5 mm in length and 2 mm in width.

CLINICAL STUDIES

Following are the results of clinical studies made on sixty-nine patients by using the above-described catheter placed in the cervix for twelve hours.

MATERIALS AND METHODS

The clinical studies were conducted in three phases as follows:

Phase 1: A group of 22 women (13 primiparous and nine multiparous) treated in an open study by intracervical administration of Prepidil gel through the illustrated double balloon catheter.

Phase 2: Included 20 women in a double blind randomized study. Ten of the women were randomized to a treatment group and received 25 ml of Prepidil gel (including 0.5 mg PGE2) intrcervically through the catheter, while the other ten women served as a control group and were given KY jelly as a placebo, via the catheter. The medication and the placebo were prepared under code in identical vials by the hospital pharmacist.

Phase 3 of the study inCluded the insertion of the illustrated catheter to 27 women without the application of any medication, but with inflation of both balloons.

All patients of this study had an aobstetrical or medical indication for induction of labor, and an unfavorable cervix (Bishop Score of four points or less). Excluded from the study were women with uterine scar, multiple pregnancy, non-vertex presentations, placental insufficiency, reptured amniotic membranes, women with a recent failed induction attempt, those with an indication for a stat delivery (i.e. fetal distress) and those with a contraindication for PG administration such as bronchial asthma). However, women with a contraindication for PG treatment were included in Phase C of the study consisting of the use of the illustrated catheter alone.

Prior to initiation of the procedure every woman underwent an ultrasonographic examination to exclude placenta previa and to confirm a vertex presentation. In addition, a non-stress test, recording of the patient's temperature and complete blood count were performed. All women underwent a pelvic examination by a senior staff member and an initial Bishop Score was obtained. The catheter was inserted either with the patient in a lithotomy position under visualization or by cervical palpation during a pelvic examination with the woman lying supine.

When both balloons enterred the cervix, the uterine balloon was inflated through the valve $V_1$, using 20 ml of sterila saline solution. The catheter was then pulled out until stopped by the uterine balloon covering the internal cervical os. At that point the cervico-vaginal balloon located at the external os was inflated via valve $V_2$ with 40 ml of sterile saline solution. The uterine balloon was further inflated with additional saline to a total volume of 40 ml (FIG. 2). The Prepidil gel was injected through the intracervical instillation valve $V_3$, followed by 1.5 ml of saline (measured to push the gel over the catheter's "dead space"). The catheter was then taped to the inner patient's thigh. The woman remained in bed rest, wth continuous external monitoring for two hours, followed by ten hours of intermittent monitoring.

Twelve hours after the insertion, the balloons were deflated and the catheter removed. At removal, or earlier if spontaneous expulsion occured, the Bishop Score was recorded again. In cases where the score was five and above, induction of labor was resumed using artificial rupture of the membranes or intravenously administered oxytocin. Women with Bishop Score of less than five points following the removal of the catheter, were induced only when a reexamination revealed a more favorable cervix, but no later than following additional 12 hours. Oxytocin was administered at a starting dose of 1 mlU/min and increased periodically to a maximum of 6 mlU/min. Data concerning timing of procedures and patient's complaints were recorded on a form prepared for this purpose. Statistical significance of the difference between groups was calculated using the Wilkinson test.

The indication for labor induction in these patients are summarized in the tables at the end of this specification. Table I shows that the majority (35 women) had post term pregnancies and a considerable number (23 women) were diangosed as having preeclampsia.

Table II shows the characteristics of the 22 women and the outcome of the induction procudure in the first phase of the study, which included the insertion of the catheter and the instillation of PGE2 gel to the endocervix. In these women, a mean increase of 5.4 points was accomplished in the Bishop Score, and 91% of them delivered vaginally. Differences between the primparous and multiparous women are depicted.

Table III compares the two groups of the double blind randomized study. The women's age, pregnancy dates and the mean parity were quite similar between the two groups. The mean Bishop Score in time "0" (1.1 and 1.2) and the change in the Bishop Score following the removal of the catheter (increasing in 5.7 and 6.0 points) were not statistically different between the treatment group and the control group, respectively.

In three of the ten women of the treatment group and in five of the ten in the control group, the catheter was spontaneously expelled during the 12 hours period following its installation. No significant pain or discomfort, nor any morbidity, was experienced by any patient of either group of women.

A mean of 9.5 hours passed from catheter introduction to the beginning of regular uterine contractions in both groups. The mean time elapsing from catheter insertion to delivery, was similar in the two patients' groups: 22.8 hours in the treatment group and 21.8 hours in the control group (Table III). Spontaneous vaginal deliveries occured in a similar rate in the two second phase groups: nine women of the treatment group, and nine of the control delivered vaginally, with one patient of every group undergoing an instrumental delivery. In addition, one woman of each study group underwent a cesarean section.

Table IV shows that the newborns in the two groups were not statistically different in their mean weights and Apgar Scores.

Table V details several characteristics of the 27 women participating in the third phase of the study, where introduction of a catheter and inflation of the balloons were not followed by any medication installed. The mean increase in Bishop Score of that group was 4.23 points. Eighty five percent of the patients delivered vaginally in this group patients. The four patients of that group who underwent a cesarean section had fetuses weighing 3360 gm to 3600 gm. Two of them had a prolonged second stage and the other two were diagnosed as having arrest of dilation with a cervix dilated to 5 cms.

Discussion

Induction of labor in a patient with an unfavorable cervix is currently attempted by intravenous administration of oxytocin or by the vaginal placement of a prostaglandin preparation. Both induction methods are associated with the initiation of uterine contractions, sometimes lasting for prolonged periods. However, the most frequent indications for labor induction at term are preeclampsia and post term pregnancy, occasionally associated with olygogydramnios (Table I). Prolonged periods of uterine contractions in these cases may cause umbilical cord compression, resulting in fetal distress. Relative placental insufficiency in these pregnancies may also be associated with fetal decompensation when prolonged uterine stimulation occurs. In addition, long hours of oxytocin infusion may lead to water overload, which may be hazardous in the case of a patient with preeclampcia.

Therefore, a preferred induction method will be the one that will lead to cervical ripening without causing uterine contractions. The technique tested in this study was initially based on applying PGE2 gel (Prepidil, Upjohn) directly and solely into the endocervical canal, by a double balloon catheter instead of a simple cannula. The two balloons confined the PGE2 gel (Prepedil, Upjohn) directly and solely into the endocervical canal, by a double balloon cathether instead of a simple cannula. The two balloons confined the PGE2 gel to the cervix itself by closing the internal and external oses. All women treated with the catheter and Prepidil had an increase of three points, or more, in the Bishop Score over 12 hours, with no discomfort or side effects. In a different article, the use of a cannula to install a PGE2 gel into the cervix resulted in a failure rate of 24.4% of the women. Those patients required a repeated instillation of PGE2, 24 hours after the first one, and in 12.2% a third instillation was given, as no change was noted in their Bishop Score.

The drawbacks of labor induction by cervical placement of PGE2 via the double balloon catheter, which kept the gel in place, close to the cervix, for long periods. The method had a very high success rate, was well tolerated by the patients, who reported no PG side effects. Conceivably, the double balloon catheter prevented spillage of the PGE2 gel onto the vagina, and avoided its absorbtion to the extraamniotic space with the possible resulting uterine hyperstimulation.

An unexpected result was obtained in the second phase of the study, involving the performance of a double blind randomized comparison of PGE2 gel versus placebo, administered via the double balloon catheter for ripening of the unripe cervix. The analysis revealed that there was no significant difference in the increase of Bishop Score between the two groups.

Induction of labor using a simple (single balloon) Foley Catheter has been discussed in the past. Ezimokhai et al (Ezimokhai M. Nwabiweli JN. The use of Foley's catheter in ripening the unfavorable cervix prior to induction of labour. Br J Obstet Gynecol 1980; 87:281–86) reported a failure rate of 20% using a Foley Catheter for instillation of Prostaglandins for induction of labor. Liberman et al (Liberman JR, Fiura B, Chaim W, Cohen A. The cervical balloon method for induction of labour. Acta Obstet Gynecol Scand 1977; 56:499–503) combined the insertion of a trancervical Foley Cathether to the intravenous administration of Oxytocin, and had better results than with a Foley Catheter inserted alone. Their reported mean insertion to labor period with the combined method was 28.4 hours, as compared to 9.5 hours obtained in the present study. In the present study, as well as in others, no cases of accidental rupture of membranes, chorioamnionitis or placental abruption were caused by the use of a catheter. The procedure was convenient and well tolerated by most women.

The findings of the present study indicate that the ripening of the cervix might have been caused by the catheter itself. The location of the two inflated balloons in both sides of the cervix might have caused mechanical pressure on the cervix, with the pressure vectors in the direction of the cervix, thus dilating.

The third part of the study, including the cervical placement of the catheter and inflation of both balloons without installing any medication, supported the finding of the double blind randomized study by demonstrating a successful ripening effect of the double balloon catheter itself without significant uterine contractions or any unwanted side effects. No significant pain or discomfort was experienced by the women treated by the catheter. Hence, the major advantage of the use of the double balloon catheter was the avoidance of medication; Prostaglandins may occasionally cause hypersensitivity and are contraindicated in patients with medical conditions such as bronchial asthma. The sole use of the catheter may also be advantageous in women with a previous uterine scar, where uterine contractions for prolonged periods are unadvisable. In addition, patients with olygohydramnios or with preeclampia may benefit from ripening of the cervix, without the need for intravenous administration of oxytocin and fluids.

The above findings suggest that the use of a double balloon catheter for ripening of an unfavorable cervix and induction of labor is an effective, safe and well tolerated novel method of labor induction. Other findings indicate that the same catheter is also effective for ripening and dilating of the uterine cervix prior to evacuation during a late-abortion procedure.

While the invention has been described with respect to one preferred embodiment, it will be appreciated that many variations may be made.

TABLE I

Indications for Labor Induction in 69 Women

| Indication | No. of women | Percent of women |
|---|---|---|
| Preeclampsia | 35 | 51 |
| Post term pregnancy | 23 | 33 |
| Chronic hypertension | 4 | 6 |
| Intrauterine growth retardation | 3 | 4 |
| Fetal malformation | 1 | 1.5 |
| Kell blood type incompatibility | 1 | 1.5 |
| Fetal hydronephrosis | 1 | 1.5 |
| Decrease in fetal movements | 1 | 1.5 |
| Total | 69 | 100 |

TABLE II

Characteristics of 22 Women Undergoing Induction of Labor by the Atad Ripener Catheter and PGE2 Gel (Phase A)

| Parity | No. of women | Mean women's age | Mean pregnancy age in weeks | Mean Bishop Score in time '0' | Mean Bishop Score at catheter removal | Mean change in Bishop Score between two exams | No. of women with successful* cervical ripening (%) | No. of women delivered vaginally (%) | Time interval from insertion to delivery in hours[a] |
|---|---|---|---|---|---|---|---|---|---|
| Nulliparous | 13 | 27 | 33.0 | 1.9 | 7.0 | 5.0 | 13 (100) | 12 (92) | 21 |
| Multiparous | 9 | 31 | 38.5 | 1.8 | 7.6 | 5.8 | 9 (100) | 8 (89) | 17 |
| TOTAL/Mean | 22 | 29 | 35.3 | 1.9 | 7.2 | 5.4 | 22 (100) | 20 (91) | 19 |

*Successful Ripening-A Bishop Score of five points and above at Catheter removal.
[a]In women delivered vaginally.

TABLE III

Characteristics of Women in the Double Blind Randomized Study of Labor Induction by the Atad Ripener Catheter and PGE2 Gel or Placebo (Phase B)

| | No. of women | Mean women's age | Mean pregnancy age in weeks | Mean parity | Mean Bishop Score in time '0' | Mean Bishop Score at catheter removal | Mean change in Bishop Score between two exams | No. of women with successful* cervical ripening (%) | No. of women with a spont. expulsion of the catheter | No. of women delivered vaginally | Time interval from insertion to delivery in hours[a] |
|---|---|---|---|---|---|---|---|---|---|---|---|
| Treatment Group | 10 | 29.2 | 40.3 | 0.9 | 1.1 | 6.8 | 5.7 | 10 (100) | 3 | 9[b] | 22.8 |
| Control Group | 10 | 29.2 | 40 | 0.8 | 1.2 | 7.2 | 6.0 | 10 (100) | 5 | 9[b] | 21.8 |

*Successful Ripening-A Bishop Score of five points and above, at Catheter removal.
[a]In women delivered vaginally.
[b]Another patient in each group was delivered by a cesarean section for non progressive labor and fetal distress.

TABLE IV

Characteristics of the Newborn of the Women Participating in the Double Blind Randomized Study of Labor Induction

| | Mean Neonatal weight in grams | Mean Apgar Score at minute '1' | Mean Apgar Score at minute '5' |
|---|---|---|---|
| Treatment Group (Catheter + PGE2) | 3219 | 8.1 | 9.5 |
| Control Group (Catheter + Placebo) | 3143 | 8.3 | 9.7 |

TABLE V

Characteristics of 27 Women Undergoing Induction of Labor by the Atad Ripener Catheter Alone

| Parity | No. of women | Mean women's age | Mean pregnancy age in weeks | Mean Bishop Score in time '0' | Mean Bishop Score at catheter removal | Mean change in Bishop Score between two exams | No. of women with successful* cervical ripening (%) | No. of women delivered vaginally (%) | Mean time from insertion to delivery in hours[a] |
|---|---|---|---|---|---|---|---|---|---|
| Nulliparous | 14 | 25.5 | 39 | 1.8 | 6.0 | 4.3 | 14 (100) | 10 (71) | 22.8 |
| Multiparous | 13 | 33 | 39 | 2.3 | 6.5 | 4.1 | 13 (100) | 13 (100) | 14.6 |
| TOTAL/Mean | 27 | 29 | 39.0 | 2.0 | 6.1 | 4.2 | 27 (100) | 23 (85) | 18.1 |

*Successful Ripening-A Bishop Score of five points and above at Catheter removal.
[a]In women delivered vaginally.

What is claimed is:

1. A catheter particularly useful for application to the cervix of the uterus in order to induce labour, comprising: a slender, flexible tube open at one end and closed at the opposite end; an inflatable distal balloon fixed to the tube at its closed end and adapted to be received in the uterus; an inflatable proximal balloon fixed to the tube at a location spaced a small distance from the distal balloon in the direction towards the open end of the tube and adapted to be received in the vagina, with the connecting portion of the tube between the two balloons passing through the cervical canal; inlet means at the open end of the tube connected by conduit means leading to the two balloons for inflating each balloon after positioned in the uterus and vagina, respectively; further inlet means at the open end of said tube for introducing a pharmaceutical substance; and an outlet opening in the connecting portion of the tube between said two balloons delivering said pharmaceutical substance to the cervical canal.

2. The catheter according to claim 1, wherein said outlet opening is oblong in shape, having a length longer than its width.

3. The catheter according to claim 1 wherein said proximal balloon is spaced about 20 mm from said distal balloon.

4. The catheter according to claim 1, wherein said flexible tube has an outer diameter of about 5.9 mm, and an inner diameter of about 3.5 mm.

5. The catheter according to claim 1, wherein said inlet means and said conduit means comprise a separate inlet and a separate conduit for each of said balloons to enable each balloon to be individually inflated.

6. The catheter according to claim 1, further including a palpable demarcation ring located on the proximal side of the proximal balloon.

7. A catheter particularly useful for the application of a pharmaceutical substance to the cervix of the uterus, comprising: a slender, flexible tube open at one end and closed at the opposite end; and inflatable distal balloon fixed to the tube at its closed end and adapted to be received in the uterus; an inflatable proximal balloon fixed to the tube at a location spaced a small distance from the distal balloon in the direction towards the open end of the tube and adapted to be received in the vagina, with the connecting portion of the tube between the two balloons passing through the cervical canal; an outlet opening formed in said connecting portion of the tube; an inlet at the open end of the tube for each balloon and connected by a conduit leading to the respective balloon for inflating each balloon after positioned in the uterus and vagina, respectively; a further inlet at the open end of the tube for introducing a pharmaceutical substance; an outlet opening in the connecting portion of the tube between the two balloons to enable the pharmaceutical substance to be introduced via the open end of the tube and to be fed via said outlet opening directly to the cervical canal; and a palpable demarcation ring located on the proximal side of the proximal balloon.

8. The catheter according to claim 7, wherein said outlet opening is oblong in shape, having a length longer than its width.

9. The catheter according to claim 7, wherein said proximal balloon is spaced about 20 mm from said distal balloon.

10. The catheter according to claim 9, wherein said flexible tube has an outer diameter of about 5.9 mm, and an inner diameter of about 3.5 mm.

11. A method of inducing labour comprising: introducing the catheter according to claim 1, into the birth canal of the female with the distal balloon located in the uterus and the proximal balloon located in the vagina; and inflating both balloons.

12. A method of applying a pharmaceutical substance directly to the cervical canal of a female, comprising: introducing the catheter according to claim 1; into the birth canal of the female with the distal balloon located in the uterus and the proximal balloon located in the vagina; and after inflating both balloons, delivering the pharmaceutical substance directly to the cervical canal via the open end of the tube and the outlet opening in the connecting portion of the tube between the two balloons.

* * * * *

UNITED STATES PATENT AND TRADEMARK OFFICE
CERTIFICATE OF CORRECTION

PATENT NO. : 4,976,692
DATED : December 11, 1990
INVENTOR(S) : Jack Atad

It is certified that error appears in the above-identified patent and that said Letters Patent is hereby corrected as shown below:

In the Abstract   Line 4, "such" should be --each--.

Lines 2-3 from end, "increases" should be --increase--.

Column 2          Line 50, "inflatible" should be --inflatable--

Column 2          Line 53, after "via", there should be inserted --a--.

Signed and Sealed this

Third Day of May, 1994

Attest:

BRUCE LEHMAN

Attesting Officer       Commissioner of Patents and Trademarks